(12) United States Patent
Eidelman

(10) Patent No.: US 8,840,835 B1
(45) Date of Patent: Sep. 23, 2014

(54) METHOD AND APPARATUS FOR STERILIZATION AND PASTEURIZATION

(76) Inventor: Gabriel Eidelman, Rockville, MD (US)

( * ) Notice: Subject to any disclaimer, the term of this patent is extended or adjusted under 35 U.S.C. 154(b) by 641 days.

(21) Appl. No.: 12/799,292

(22) Filed: Apr. 20, 2010

(51) Int. Cl.
*A61L 2/02* (2006.01)
*A23L 1/025* (2006.01)

(52) U.S. Cl.
CPC *A61L 2/02* (2013.01); *A23L 1/0252* (2013.01)
USPC .......................... 422/20; 426/238; 204/157.15

(58) Field of Classification Search
CPC .......... A61L 2/02; A61L 2/025; A23L 1/0252
USPC ................. 204/157.15; 422/20; 426/237, 238
See application file for complete search history.

(56) References Cited

U.S. PATENT DOCUMENTS

| | | | |
|---|---|---|---|
| 5,256,430 A * | 10/1993 | Suzuki et al. | 426/238 |
| 5,273,766 A | 12/1993 | Long | |
| 5,328,403 A * | 7/1994 | Long | 426/238 |
| 5,519,670 A * | 5/1996 | Walter | 422/20 |
| 5,588,357 A | 12/1996 | Tomikawa et al. | |
| 6,264,543 B1 | 7/2001 | Garcia et al. | |
| 7,244,459 B2 | 7/2007 | Long et al. | |
| 2008/0056937 A1 * | 3/2008 | Cordemans De Meulenaer et al. | 422/20 |

OTHER PUBLICATIONS

N.C. Carpita, "Tensile Strength of Cell Walls of Living Cells"; Plant Physiol., 1985, vol. 79, pp. 485-488.
S.M. Loske, et al., "Repeated Application of Shock Waves as a Possible Method of Food Preservation", Shock Waves, 1999, vol. 9, pp. 49-55.
K. Teshima et al., "Biomechanical Effects of Shock Waves on *Escherichia coli* and Aphage DNA", Shock Waves, 1995, vol. 4, pp. 293-297.
J. Barthel et al., "Biomechanical Cellular Response Due to Shock Waves", Proc. 26th Army Science Conference, Orlando, FL, 2008, pp. 1-7.
A. Abe, et al., "The Effect of Shock Pressures on the inactivation of a Marine Vibrio sp.", Shock Waves, 2007, vol. 17, pp. 143-151.

* cited by examiner

*Primary Examiner* — Timothy Cleveland

(57) ABSTRACT

A method for sterilization and pasteurization includes providing an apparatus including a shock generation section; a sterilization section; and a membrane provided there between; placing media contaminated with microorganisms into the sterilization section; introducing a detonable mixture into the shock generation section; causing formation of at least one of a shock wave and an acoustic wave by igniting the detonable mixture, so that the at least one of a shock wave and an acoustic wave impinges on the membrane and is transmitted thereby into the sterilization section, and so that the media is sterilized or pasteurized by the at least one of a shock wave and an acoustic wave that will kill at least some of the microorganisms; venting the shock generation section via a pressure relief valve; and repeating to achieve a pre-determined degree of sterilization or pasteurization.

12 Claims, 7 Drawing Sheets

METHOD AND APPARATUS FOR STERILIZATION AND PASTEURIZATION

BACKGROUND OF THE INVENTION

1. Field of the Invention

The present invention relates to method and apparatus for sterilization and/or pasteurization of consumables including water, liquid food or food submerged into liquids including juices, parenteral products, milk, yogurt, meat parts in water or other liquid, raw oysters in water, and so forth.

2. Description of Related Art

Use of shockwaves for sterilization is known. U.S. Pat. No. 5,588,357 to H. Tomikawa et al. discloses utilization of shock waves created by rapid electric discharge through a conducting wire in liquid for food sterilization. U.S. Pat. No. 6,264,543 discloses use of an array of electromechanical transducers to create shockwaves in liquid for the purpose of tenderization and sterilization of meat. U.S. Pat. No. 5,273,766 discloses use of solid explosives detonated in water for producing strong shockwaves for meat tenderization.

Food sterilization and pasteurization processes kill a significant number of harmful bacteria making food safe for consumption and extending its shelf life. Using shockwaves for sterilization and pasteurization of liquid food or food immersed in liquid allows food sterilization without significant elevation of temperature, which can affect food taste, texture and appearance.

Bacteria can be classified in two major groups, gram-positive and gram-negative. Gram-positive bacteria cell walls are simple in structure, but have thick peptidoglycan layers (10-20 layers thick) which make the cell walls strong and robust. Gram-negative cells have complex cell wall structures but much thinner peptidoglycan layers (only 1-2 layers thick). Therefore, the gram-positive cells are stronger, less likely to be broken mechanically, and are less permeable than the gram-negative cells. At the same time gram-positive cells, being larger, are more susceptible to sheer stress caused by a shockwave. Tensile strengths of cell walls of a number of bacteria were evaluated using rapid decompression experiments (see Carpita N. C., "Tensile Strength of Cell Walls of Living Cells", *Plant Physiol.*, Vol. 79, pgs. 485-488, (1985)). In these experiments it was found that liquid cultures of the bacterium *Salmonella typhimurium* (gram-negative) were disrupted at a pressure drop of ~10 MPa. *Blastocladiella emersonii* (aquatic fungus), which has a wall thickness about two orders of magnitude larger than *Salmonella*, was disrupted with an even lower pressure drop of 6.5 MPa. These pressures are much lower than pressures used in the High Pressure Processing (HPP) method for sterilization of food products indicating that rapid compression/decompression, that will be typical for the shockwave effect, is an effective technique for sterilization. In a separate study it was also shown that *Escherichia coli* can be killed using an electrohydraulic shock-wave generator typically used for extracorporeal lithotripsy (see A. M. Loske et al., "Repeated application of shock waves as possible method for food preservation", *Shock Waves*, Vol. 9, pgs. 49-55 (1999)). In this study it was determined that sterilization occurred only after multiple exposures to shock waves with the peak pressure of ~50 MPa.

A number of techniques exist for generation of intensive shock waves in liquids. These methods include electric arc discharge, wire explosion, and projectile impact. The biomechanical effects of shock waves have been studied for the killing of bacteria and general food sterilization. See K. Teshima et al., "Biomechanical Effects of Shockwaves on *Escherichia Coli* and Aphage DNA", *Shock Waves*, Vol. 4, pgs. 293-297 (1995); J. Barthel et al., "Biomechanical and Biochemical Cellular Response Due to Shock Waves", *Proc. 26th Army Science Conference*, Orlando, Fla., (2008); and A. Abe et al., "The Effect of Shock Pressures on the Inactivation of a Marine *Vibrio* sp.", *Shock Waves*, Vol. 17, pgs. 143-151 (2007).

However, despite the clearly demonstrated effectiveness of using high-intensity shock waves for killing bacteria, there are no practical applications of this effect. The main problem is lack of capability of creating shockwaves of needed intensity in industrial settings that is compatible with food or parenteral products processing. Use of electromechanical transducers will require shockwaves focused in a small volume to attain pressure levels required for killing bacteria, thus making sterilization of large amounts of food impractical. Use of exploding wire as disclosed in U.S. Pat. No. 5,588,357 is inefficient and requires a large capacitor as an energy source for rapid vaporization of the wire that creates the shockwave. Also food would need to be insolated in plastic to avoid contact with metal particles generated by the exploded wire.

Use of explosives, as disclosed in U.S. Pat. No. 5,273,766 for meat tenderizing, can generate strong shockwaves in large volumes. However, during processing, food needs to be insolated from toxic explosive products. Also, use of explosives in an industrial environment is not desirable because of safety and environmental concerns.

Thus, there is a critical need for efficient generation of high intensity shockwaves for food sterilization and pasteurization. The present invention contemplates elimination of the drawbacks associated with prior art of generation of shockwaves for sterilization and provides a method and apparatus for sterilization and pasteurization that is critical for practical application of shockwaves to sterilization and pasteurization. The present invention will also allow use of scalable sterilization apparatuses in households or in industry.

It is therefore the object of the present invention to provide a method and apparatus for sterilization or pasteurization of water, liquid food or food immersed in liquid such as juices, parenteral fluids, milk, shellfish, meat parts, ready to eat meals composed of cooked or raw produce, avocado paste, and similar products.

It is another object of the present invention to provide a method and apparatus for sterilization or pasteurization of food products without significant temperature rise during processing that can affect its nutritional or sensory quality.

A further object of the present invention is to provide a method and apparatus for sterilization or pasteurization that can be scaled for use in households or in industry.

Another object of the invention is to provide a method and apparatus that can be used for batch or continuous sterilization or pasteurization processing of food products.

Another object of the invention is to provide a method and apparatus for rapid and energy efficient sterilization of water and consumer products that can be immersed in liquid such as medical devices.

SUMMARY OF THE INVENTION

These and other objects of the present invention are achieved by providing a method and apparatus that includes the steps of generating high pressure shockwaves or acoustic waves in a shock generation section of the apparatus, transmitting these waves to a sterilization section of the apparatus through a membrane, and killing microorganisms residing in the media contained in the sterilization section of the apparatus by means of incident and reflected high intensity shockwaves and/or acoustic waves that are transmitted from the shock generation section to the liquid-containing sterilization section. The process is conducted at ambient temperatures or with minimal heat where exposure of food to high intensity shockwaves, with peak pressures between 10 MPa to 200 MPa and positive phase duration of 5 μsec to 100 μsec, that will kill all or a substantial number of microorganisms. Since water, juices and similar liquids have very small compressibility, the microorganism killing shockwaves will not lead to a substantial change of temperature of the liquids. Also, the shock intensity can be modulated not to cause change in food texture if not desired. Both shock generation and sterilization sections of the apparatus can be designed to make more efficient use of shockwave energy and to kill bacteria more efficiently. As a result of exposure to high intensity shockwave treatment bacteria such as *Vibrio Vulnificus, E. coli, Salmonella typhimurium, Staphylococcus aureus* and other common pathogens will be killed without substantially affecting the sensory qualities of the food products.

Following the shock generation stage of the process, the reaction products can be discharged through a pressure relief valve into the atmosphere or a products collection tank. After discharge of the detonation products the process can be repeated as many times as needed for killing bacteria and other microorganisms.

In another embodiment a sterilization apparatus comprises a shock generation chamber, valves or other means for controlled injection of fuel and oxidizer, igniter, a membrane that seals the shock generation chamber, and sterilization chamber containing food or other products that are to be sterilized. In this embodiment, the size of the shock generation chamber can be from 10 $cm^3$ to 1000 $m^3$, but usually from 100 $cm^3$ to 1 $m^3$ and a sterilization chamber can be from 10 $cm^3$ to 1000 $m^3$, but usually from 100 $cm^3$ to 10 $m^3$. Such a wide range of scales of implementation facilitated by using a detonable mixture that can be injected into the shock generation section of an apparatus that is designed to contain detonation products after detonation and is critical for industrial applications.

In another embodiment, a sterilization apparatus comprises a shock generation section, valves or other means for controlled injection of fuel and oxidizer, igniter, and a pressure relief valve. The shock generation section is enclosed within the sterilization section. In this embodiment the food, or other material in the sterilization section, is sterilized by the shockwaves transmitted through walls of the shock generation section and reflected by the walls of the sterilization section. To generate high pressure and shockwaves in the sterilization section the detonable mixture injected into the shock generation section before detonation will have an average material density larger than 1 $kg/m^3$ and smaller than 3000 $kg/m^3$. After detonation the shockwave transmitted through the walls of the shock generation section will have a peak pressure of 10 MPa to 1000 MPa and shockwave positive phase duration of 5 μsec to 100 μsec, which will kill a substantial number of microorganisms in the sterilization section, thus pasteurizing or sterilizing food or other materials in this section. Such a wide range of pressures can be achieved by injecting suitable detonable mixture into the shock generation section of an apparatus that is designed to contain detonation products after detonation and is critical for industrial applications.

In another embodiment, a sterilization apparatus comprises a shock generation section and sterilization section. In this embodiment, a detonable mixture in the shock generation section is produced by electrolysis of water based electrolyte. The method comprises supplying electrical power to decompose water in an electrolysis cell located inside or outside of the shock generation section. Water decomposition generates oxygen and hydrogen gases that fill the volume of the shock generation section. These gases are mixed and ignited. Ignition of the hydrogen/oxygen mixture will generate a shockwave in the shock generation section. This shockwave will transmit through the walls or wall of the shock generation section into media contained in the sterilization section. When the transmitted shockwave is of sufficient intensity it will kill bacteria and other microorganisms contained in the media located in the sterilization section. After detonation the detonation products, which will be composed primarily of water vapor, will condense into liquid water that can be used in the next sterilization cycle. Alternatively, the water vapor generated by the detonation process can be evacuated from the shock generation chamber via a gas relief valve and liquid water can be injected into the water electrolysis section of the apparatus for use in the next sterilization cycle. This embodiment of the sterilization apparatus will allow operation without use of reactive gases and will be particularly attractive for individual household use.

In another embodiment, a sterilization apparatus comprises of two or more shock generation sections that are inserted within a single sterilization section. In this embodiment a detonable mixture is injected simultaneously or with a time delay into shock generation sections where reactions are initiated simultaneously or with a time delay. Multiple shock generation sections will create multiple shock waves or acoustic waves that will propagate into the sterilization section causing sterilization and/or pasteurization of the media located in this section.

The process' sterilization cycle can be applied a single or multiple times depending on shock sterilization efficiency, type of food sterilized, degree of contamination with pathogens, and types of pathogens.

BRIEF DESCRIPTION OF THE DRAWINGS

The present invention will now be described in more detail with reference to preferred embodiments of the invention, given only by way of example, and illustrated in the accompanying drawings in which.

DETAILED DESCRIPTION OF THE INVENTION

Figure 1:
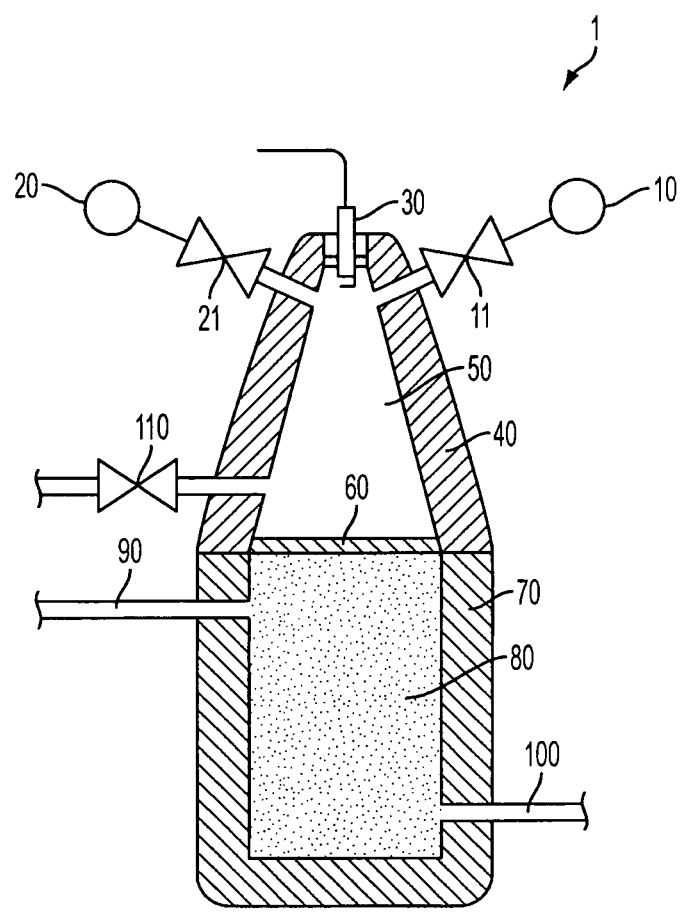
FIG. 1 is a schematic illustration of the apparatus for sterilization and pasteurization according to one embodiment of the present invention in which liquid to be sterilized is supplied continuously into a cylindrical sterilization section and the shock generation section is in the form of a conical chamber.

Here, and in the following claims, terms are defined as follows.

"Shock generation section" or the "first section" is the section of the apparatus where shockwaves are generated as a result of chemical reaction.

"Sterilization section" or the "second section" is the section of the apparatus where the media or food is contained and sterilized.

"Shockwave", "shockwaves", "pressure wave" when used in relation to processes in the shock generation section of the apparatus all describe gas dynamic shock waves or waves created by reaction of a detonable mixture that propagates with supersonic speed.

"Shockwave", "shockwaves", "pressure wave" when used in relation to processes in the sterilization section of the apparatus all describe hydrodynamic shock waves or acoustic waves that propagate with sonic or supersonic speed in liquid that is being sterilized.

"Detonation", "detonation process" are similar terms and are used herein to describe a physical and chemical phenomena characterized by a rapid chemical reaction that leads to the creation of a shockwave, shockwaves or pressure waves. When used in relation to the process within the first section, i.e., the shock generation section, of the apparatus these terms are used to describe a reactive process that generates a shockwave, shockwaves or pressure waves. It is understood that, as a function of chemical composition, quantities, initial pressure and temperature, different types of chemical reactions including deflagration, detonation, and transition from deflagration to detonation, rapid decomposition and combination thereof will lead to rapid pressurization of shock generation section and generation of shockwaves or pressure waves.

"Detonable mixture" as used herein, refers to single or multiple reactants that can undergo rapid chemical reactions including detonation, deflagration, rapid decomposition or combination thereof creating a shockwave or pressure wave. One example of a detonable mixture is the mixture of oxygen, hydrogen and nitrogen gases. Another example of a detonable mixture is a monopropellant such as nitrobenzene or nitroglycerin. Another example of a detonable mixture is high concentration hydrogen peroxide that can undergo explosive decomposition after injection into the shock generation section of the apparatus. Selection of a suitable fuel and oxidizer or a single reactant to form the detonable mixture will be apparent to persons skilled in the art. Non-limiting examples of fuel reactants that can be used to form a detonable mixture include kerosene, gasoline, methane, natural gas, acetylene, and propylene. Non-limiting examples of oxidizer reactants that can be used to form the detonable mixture include oxygen, air, a mixture of oxygen and air, a mixture of oxygen and one or more inert gases such as nitrogen, argon or helium.

"Sterilized media", "sterilized liquid" as used herein, refers to a liquid, a multiphase liquid-solid and gas suspension, a paste and other forms of material that can transmit hydrodynamic shock or acoustic waves that cause sterilization and/or pasteurization. One example of a liquid to be sterilized is milk and milk products such as yogurt and kefir. Another example of media to be sterilized is guacamole paste. Another example of media to be sterilized are pieces of meat suspended in water or broth. Another example of sterilized media is fresh oyster suspended in water. Another example of media to be sterilized is water. Another example of media to be sterilized is fruit juice. Another example is sterilization of parenteral dosage forms before use to assure pathogen-free injectable products. Another example of media to be sterilized is vegetable salad suspended in water.

"Sterilization", "pasteurization", "pasteurization and sterilization", and "pasteurization or sterilization" are used interchangeably meaning a total or substantial reduction in bacteria, fungus and other harmful microorganisms.

"Impedance" means "acoustic impedance" that can be calculated by multiplying density and sound speed of the media.

"Membrane" is a part of the shock generation section of the apparatus that transmits shock waves or acoustic waves from the shock generation section into the sterilization section of the device.

Referring now to the invention in more detail, FIG. 1 schematically illustrates an apparatus 1 for sterilization and pasteurization according to one embodiment of the present invention. The apparatus is configured for continuous sterilization processing. The apparatus has a first section 40 that is a shock generation section 40 into which oxidizer is injected from an oxidizer storage tank 10 through a control valve 11 and fuel is injected from a fuel storage tank 20 through a fuel control valve 21. The shock generation section 40 also includes spark plug 30, pressure relief valve 110 and shock transmitting membrane 60. The apparatus 1 also has a second section 70 that is a sterilization section 70 filled with media 80 to be sterilized, which has inlet 90 and outlet 100 that control the flow of media 80 through the sterilization section 70. Sterilization section 70 is attached to the shock generation section 40 in such a way that the external surface of the membrane 60 that is facing the media 80 to be sterilized, such as fruit juice, is fully immersed into the media 80. This embodiment can operate with continuous flow of media 80 through the sterilization section 70 where it gets exposed to intermittent shock waves or high intensity acoustic waves that kill microorganisms.

One non-limiting example of the sterilization apparatus design shown schematically in FIG. 1 has a conically-shaped shock generation chamber 40 with a diverging geometry from a spark plug 30 to membrane 60, with an internal volume base diameter in the area of membrane 60 of 20 cm and an internal height of 20 cm resulting in an internal volume of the shock generation section 40 of ~2100 cm$^3$. The sterilization section 70 is cylindrical with an internal diameter of 20 cm and an internal height of 20 cm resulting in ~6300 cm$^3$ internal volume. The walls of sterilization section 70 are made of ~1.5 cm thick high strength steel. The walls of sterilization section 70 are made of ~2 cm thick tungsten-carbide-cobalt cermet. The membrane 60 is made from 0.5 cm thick high strength steel and the membrane is welded to the walls of the shock generation section 40.

In a non-limiting example of the sterilization apparatus operation, according to one embodiment of the present invention, the operation of apparatus 1 schematically shown in FIG. 1 starts with the injection of media 80 that will be sterilized, e.g., milk, yogurt, juice or other liquid or paste food stuff, into an internal volume of the sterilization chamber 70 through inlet 90. When the chamber is full and the external surface of membrane 60 is fully immersed in media 80 to be sterilized, fuel and oxidizer are injected into the internal volume of the shock generation section 40. The fuel and oxidizer are selected so that the mixture is detonable and their injection through control valves 21 and 11, respectively, is metered so that the resulting detonable mixture 50, upon detonation, will form shock waves of sufficient intensity that will result in sterilization of media 80 in the sterilization section 70 of the apparatus 1. Injection of a sufficient amount of detonable mixture 50 is followed by the ignition of this mixture 50 by a spark plug 30 that initiates a detonation wave. The time sequence of injection of fuel and oxidizer and ignition of the mixture 50 can be suitably selected by persons skilled in the art with the aid of no more than routine experimentation. After ignition by a spark plug 30, the detonation wave propagates through the volume of the shock generation section 40 and reaches the membrane 60 separating the shock generation section 40 and the sterilization section 70. A part of the shock wave reflects back into the shock generation section 40 and another part passes through the interface, i.e., membrane 60, into the sterilization section 70. The shock transmitted into the sterilization section 70 of the apparatus 1 of the current invention will cause lysing of the cell walls of bacteria, sterilizing the media 80, such as a suspension of food immersed in media 80. As the processed suspension is removed from the sterilization section 70 through outlet 100, fresh media 80 (foodstuff suspension 80) is introduced in the inlet 90. Detonation products are removed from the internal volume of the shock generation section 40 via the pressure relief valve 110 and fresh reactants are then introduced in the shock generation section 40 and the process is repeated. A continuous flow of media 80 through the sterilization section 70 can be sterilized by intermittent shock waves produced by the shock generation section 40 wherein the flaw rate of media 80 to be sterilized through the sterilized section 70 can be suitably selected by persons skilled in the art with the aid of no more than routine experimentation to allow at least one exposure of the media 80 to the shockwaves.

The amounts of energy transferred and reflected will be a function of the physical parameters of the detonation wave, the membrane 60, and the media 80 in the sterilization section 70. Parameters of the detonation mixture 50, membrane 60, and media 80 can be suitably selected by persons skilled in the art with the aid of no more than routine experimentation in such a way that a substantial portion of shockwave energy generated in the shock generation section 40 is transmitted into the sterilization section 70.

In the embodiments shown in FIGS. 1 through 4 and 6 through 7, the walls of shock generation section 40 and sterilization section 70 of the apparatus 1 of the present invention can be, but not necessarily be, constructed of high density and high impedance material of sufficient thickness that will facilitate reflection of the shockwaves and acoustic waves so that reflected waves could be utilized for killing microorganisms in the media 80 to be sterilized. The membrane 60 of the apparatus 1 of the present invention can be, but not necessarily be, constructed to sustain the pressure load produced by repeated detonation in the shock generation section 40 and have minimal thickness and impedance to allow transmission of the shock waves from the shock generation section 40 to sterilization section 70 of the apparatus 1. Thickness of the membrane will be a function of pressure in the shock generation section and material strength of the membrane material, and may range from 0.5 mm to 50 cm. In the embodiments shown in FIGS. 5 and 8 where the walls of the shock generation section 40 are immersed into the sterilization section 70, the materials selected for the shock generation section 40 should be selected to contain detonations and allow for efficient transmission of shockwaves into the media 80. Materials, wall thickness and wall geometry of shock generation section 40, sterilization section 70, and membrane 60 of the apparatus 1 according to the present invention can be suitably selected by persons skilled in the art with the aid of no more than routine experimentation. To prevent the membrane and walls of the shock generation section 40 from excessive heating in the apparatus 1 according to the present invention, standard cooling methods can be suitably selected by persons skilled in the art with the aid of no more than routine experimentation. As non-limiting examples of cooling, one can time the detonations so excessive heat is removed to the surroundings through natural convection or, in the embodiment illustrated in FIGS. 5 and 8, design the flow rate of the media 80 so that heat is absorbed by the media 80 without a significant increase of its temperature.

Figure 2:
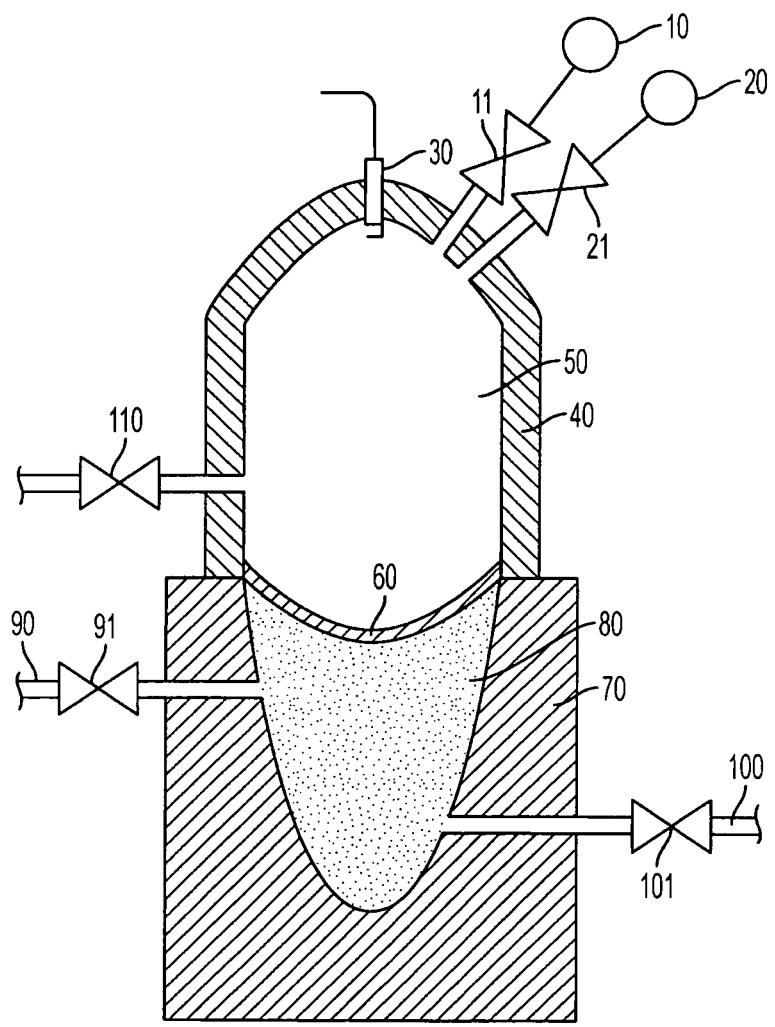
FIG. 2 is a schematic illustration of the apparatus for sterilization and pasteurization according to another embodiment of the present invention in which liquid to be sterilized is supplied intermittently into a sterilization chamber and both the shock generation and sterilization section have a combination of hemispherical and cylindrical cross sections.

FIG. 2 schematically illustrates an embodiment in which shock generation section 40 has a larger volume than sterilization section 70 and its geometry is cylindrical with a hemispherical section. The membrane 60 geometry is hemispherical and the sterilization section 70 has a cross section that is parabolic. The sterilization section 70 and media flow inlet 90 and outlet 100 are equipped with flow control valves 91 and 101, respectively. All other components of the apparatus 1 are as described above with reference to the embodiment of FIG. 1. As discussed above, the dimensions (e.g., diameter and volume) and geometries of the shock generation section 40 and sterilization section 70, as well as the properties of the materials used, can be manipulated to influence processing conditions. Construction shown in FIG. 2 with properly selected detonation conditions will allow for the exposure of the media 80 to high intensity shock or acoustic waves. This embodiment can operate with continuous or intermittent flow of media 80 through the sterilization section 70 controlled by flow control valves 91 and 101 where it gets exposed to intermittent shock waves or high intensity acoustic waves that kill microorganisms. The timing of the media 80 injection into the volume of the sterilization section 70, fuel 10 and oxidizer 20 injection into the volume of shock generation section 40, and detonation ignition by a spark plug 30 can be suitably selected by persons skilled in the art with the aid of no more than routine experimentation to allow single or multiple exposures of the media 80 to the shockwaves that will cause its sterilization and/or pasteurization.

Figure 3:
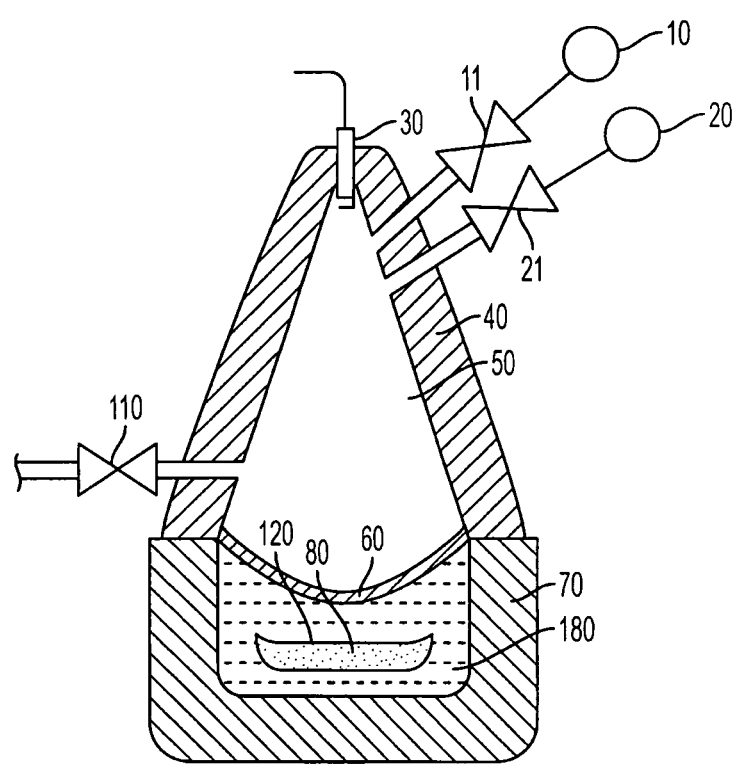
FIG. 3 is a schematic illustration of the apparatus for sterilization and pasteurization according to another embodiment of the present invention in which a media to be sterilized is placed in a container which is then placed in the liquid of the sterilization section.

FIG. 3 schematically illustrates another embodiment in which the cross section of the shock generation section 40 of the apparatus 1 has parabolic geometry and media 80 to be sterilized is placed in a container 120 which is then placed in a liquid 180, for example, water, of the sterilization chamber 70. This embodiment can operate in a batch mode where a container 120 that contains media 80 to be sterilized is placed in liquid 180 and then the sterilization section 70 is aligned with the shock generation section 40 of the apparatus 1. It is foreseen that liquid 180 can be selected without limitation to have low impedance to facilitate more efficient shockwave energy transmission from the shock generation section to sterilization section.

Figure 4:
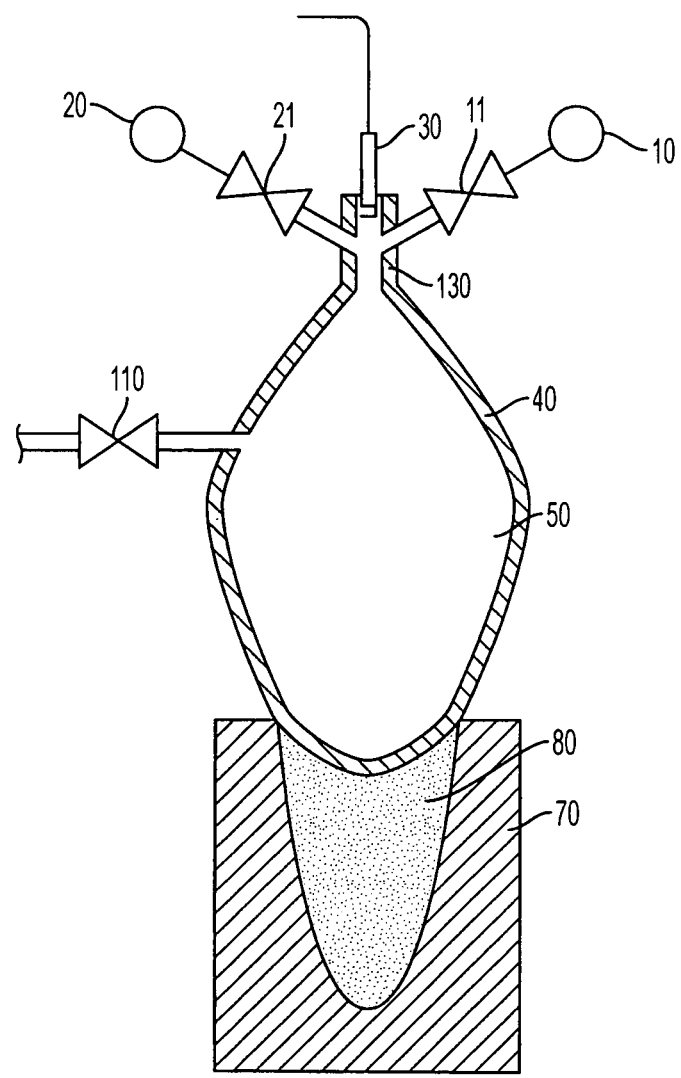
FIG. 4 is a schematic illustration of the apparatus for sterilization and pasteurization according to another embodiment of the present invention in which the shock generation section contains a detonation initiation tube and has a diverging/converging cross section.

FIG. 4 schematically illustrates another embodiment in which the cross section of the shock generation section 40 of the apparatus 1 has diverging-converging geometry and a cylindrical section 130 that is designed to facilitate more effective transition to detonation in the shock generation section 40 of the apparatus 1. The embodiment schematically illustrated in FIG. 4 can be operated in a batch operation mode where media 80 to be sterilized is filled into the sterilization section 70, the sterilization section 70 is then aligned with the shock generation section 40 and exposed to shock waves transmitted through the section of the wall of shock generation section that is immersed into media 80. That is, in this embodiment, membrane 60 is an integral extension of the shock generation section 40. Transmitted shockwaves or acoustic waves will kill microorganisms after detonation of reactants, i.e., detonable mixture 50, in the shock generation section 40. After that sterilized media 80 is emptied into a container (not shown) and the new media 80 is filled into the sterilization section 70. Illustrated in FIG. 4, sterilization section 70 has a converging geometry that will facilitate focusing of shockwaves and acoustic waves transmitted into section 70 that will enhance sterilization effect.

Figure 5:
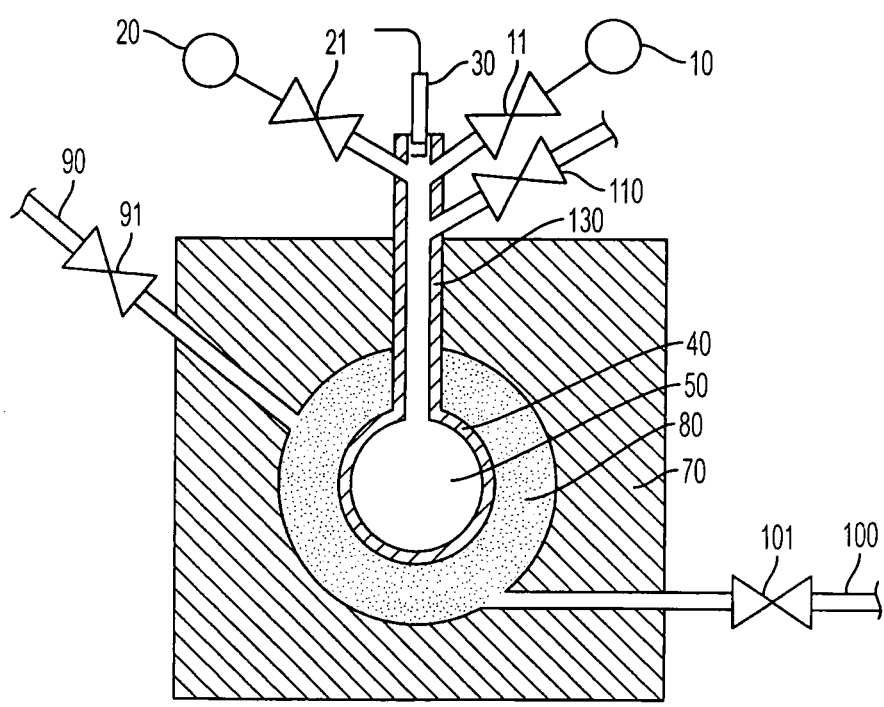
FIG. 5 is a schematic illustration of the apparatus for sterilization and pasteurization according to another embodiment of the present invention in which the shock generation section is mostly submersed into media to be sterilized in the sterilization section.

FIG. 5 schematically illustrates another embodiment in which the cross section of the shock generation section 40 is mostly spherical with a cylindrical part 130 for initiation of shock waves. The shock generation section 40 is inserted into the sterilization section 70 which has a spherical inner volume that is filled with medium 80. The media 80 is supplied either continuously or intermittently into the sterilization chamber 70 via inlet 90 and removed through outlet 100. The configuration schematically illustrated in FIG. 5 will be particularly effective for sterilization because shock waves generated by detonations will emit into the sterilization section 70 through spherical walls of the shock generation section 40 propagating through a large surface. The media 80 to be sterilized will be located in a gap between the outer walls of the shock generation section 40 and the inner walls of the sterilization section 70 and will be exposed to strong acoustic waves or shock wave more uniformly than in other designs shown in FIGS. 1 through 4. In a non-limiting example of the sterilization apparatus schematically shown in FIG. 5, the shock generation section 40 will have a 10 cm diameter and a sterilization section 70 of 16 cm diameter. The cylindrical initiation section 130 will have 1 cm ID and will be 10 cm long. In this case, the volume of the shock generation section 40 will be ~500 cm$^3$ and the volume of the sterilization section 70 will be ~1600 cm$^3$. In this non-limiting example, the apparatus will be capable of sterilization of ~140 tons of media 80, e.g., juice, per day when it flows through the sterilization volume at a rate of 1.6 l/sec. To facilitate sterilization at this rate, the shock generation section 40 will produce at least one detonation per second that will generate pressure waves that will kill microorganisms. Sterilization will occur in a ~3 cm wide gap between the walls of shock generation section 40 and sterilization section 70.

Figure 6:
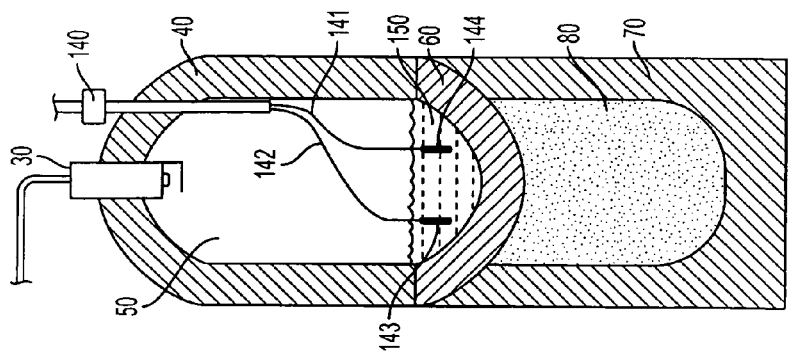
FIG. 6 is a schematic illustration of the apparatus for sterilization and pasteurization according to another embodiment of the present invention in which detonable mixture used in the shock generation section is produced by electrolysis of water contained in this section.

FIG. 6 schematically illustrates another embodiment in which the detonable mixture 50 is a hydrogen-oxygen gas mixture that is generated by electrolysis of water-based electrolyte 150. Non-limiting examples of water based electrolytes are: water/sulfuric acid ($H_2SO_4$), water/potassium hydroxide (KOH), and water/sodium hydroxide (NaOH) electrolytes. In this embodiment, an electric voltage is conducted through electrical lines 141 and 142 via a sealed conduit 140. Water electrolysis cell with cathode 142 and anode 141 is immersed into water-based electrolyte 150 and will decompose water to hydrogen gas and oxygen gas upon supply of sufficient electrical energy. After a sufficient amount of detonable mixture 50 is generated, the mixture 50 is ignited by a spark plug 30 generating a detonation and shockwave that sterilizes the media 80 in the sterilization section 70 of the apparatus 1. After detonation, the detonation products that will be mostly composed of water vapor can be condensed into water through cooling of the shock generation chamber 40 and the process can be repeated. A critical advantage of this embodiment is that it will not require a supply of detonable mixture 50 and that the detonation product is not vented into the atmosphere. Thus, this type of device will be particularly attractive for home use. The apparatus 1 shown schematically in FIG. 6 can be implemented for continuous, intermittent or batch sterilization processing. The shockwave pressure generated in the device schematically shown in FIG. 6 will be a function of density and pressure of the detonable mixture that will be generated as a result of electrolysis. It is foreseen that the density of the detonable mixture produced by electrolysis prior to initiation may range from 0.1 to 1000 kg/m$^3$.

Figure 7:
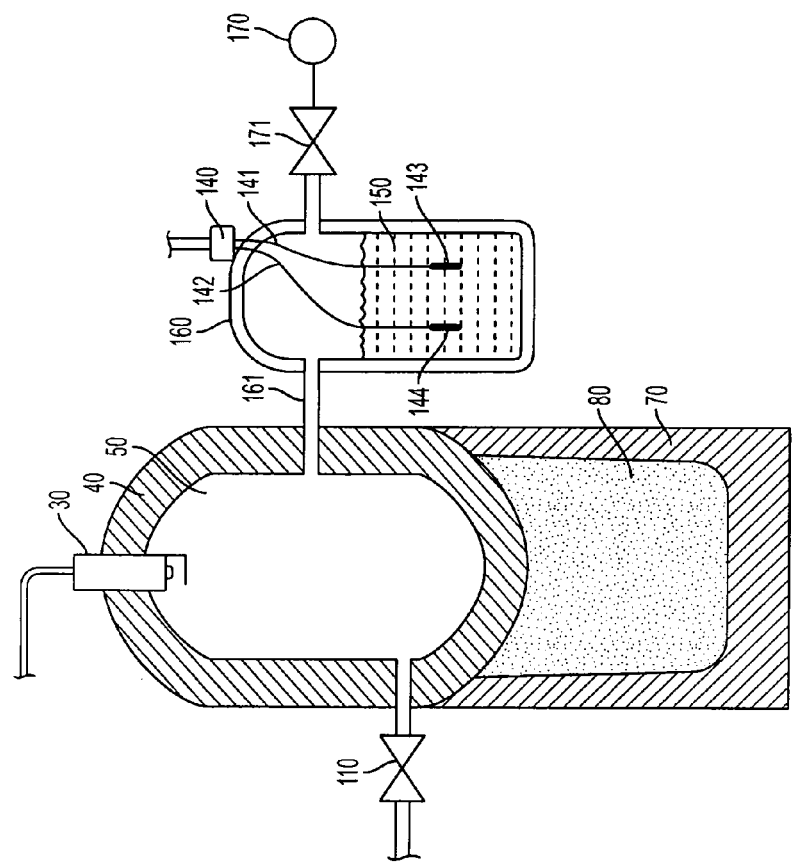
FIG. 7 is a schematic illustration of the apparatus for sterilization and pasteurization according to another embodiment of the present invention in which detonable mixture used in the shock generation section is produced by electrolysis of water in a separate water electrolysis section.

FIG. 7 schematically illustrates another embodiment of the apparatus 1 according to the present invention that is also based on the generation of detonable mixture 50 through water electrolysis as shown in the embodiment in FIG. 6. However, the electrolysis of water is done in a separate electrolysis section 160 that is connected to the internal volume of the shock generation section 40 through a gas conduit 161. Also, in this embodiment, the detonation products are vented through a relief valve 110 and water-based electrolyte 150 is supplied to the electrolysis section 160 from a water-based electrolyte tank 170 through a flow control valve 171. An advantage of this embodiment is that it will require supply of only water-based electrolyte 150 and electricity for generation of shock waves and will not require cooling for water regeneration as in the embodiment shown in FIG. 6. The apparatus 1 shown schematically in FIG. 7 can be implemented for continuous, intermittent or batch sterilization processing. It is foreseen that the detonable 50 mixture can be supplied by multiple electrolysis sections 160 or a single electrolysis section 160 can supply detonable mixture into multiple shock generation sections 40.

Figure 8:
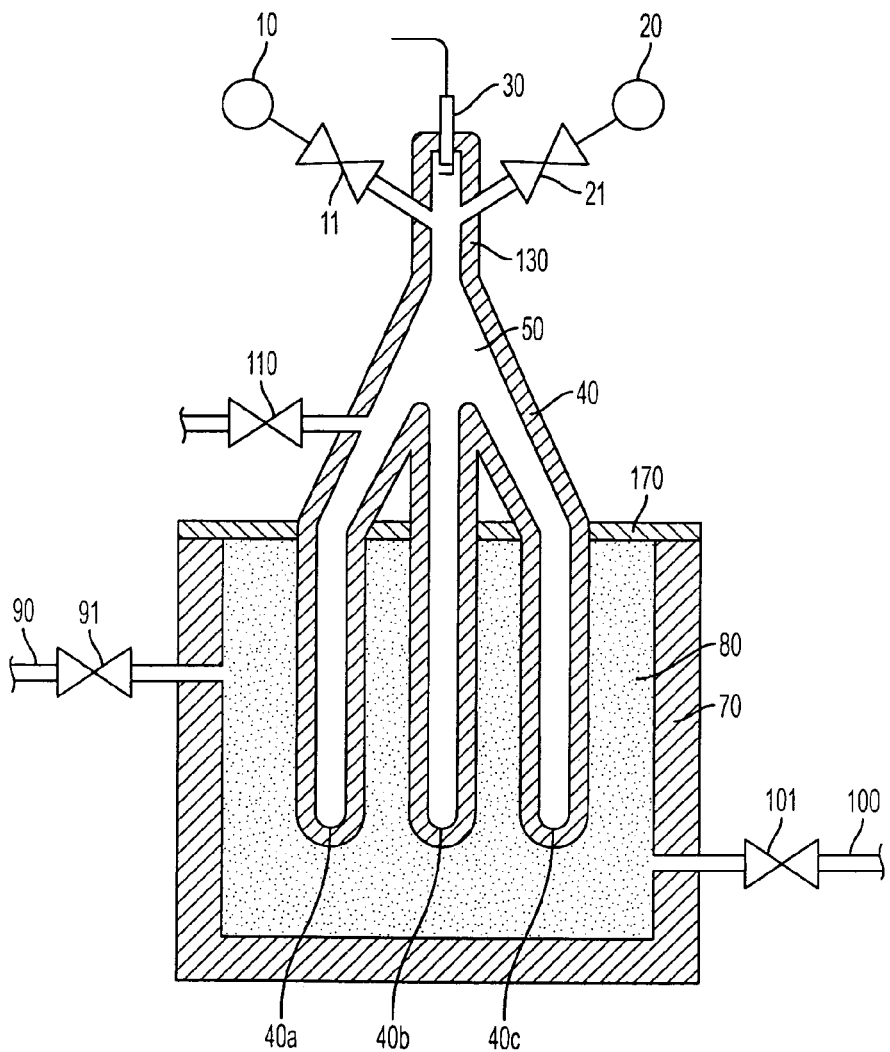
FIG. 8 is a schematic illustration of the apparatus for sterilization and pasteurization according to another embodiment of the present invention in which the shock generation section is split into multiple, connected, closed-ended conduits that are immersed into the sterilization section

FIG. 8 schematically illustrates another embodiment of the apparatus 1 according to the present invention. The apparatus 1 consists of a shock generation section 40 that is formed by multiple cylindrical extensions 40a,40b,40c stemming from and connected to a single reactant initiation tube 130. The cylindrical extensions 40a,40b,40c terminate in semispherical end caps as shown in FIG. 8. The cylindrical extensions 40a,40b,40c will be immersed into the media 80 of the sterilization section 70. Oxidizer 10 and fuel 20 are injected through control valves 11 and 21, respectively, and fill the internal volume of the shock generation section 40 with detonable mixture 50. Ignition of the detonable mixture 50 by spark plug 30 will initiate the detonation wave that will propagate into all cylindrical extensions 40a,40b,40c generating shockwaves that will partially transmit into media 80. Multiple extensions 40a,40b,40c will produce shock waves and acoustic waves that will emit essentially simultaneously from multiple sources. Constructive and destructive interference of these high intensity waves will produce an environment that will be effective for media 80 sterilization. The invention embodiment shown in FIG. 8 will also be beneficial because it will allow uniform exposure of the media 80 to shock waves and acoustic waves. The apparatus 1 shown schematically in FIG. 8 can be implemented for continuous, intermittent or batch sterilization processing.

The apparatus 1 for sterilization and pasteurization of the present invention has the utility of producing high intensity shock waves and/or acoustic waves in media 80 to be sterilized that are required for killing harmful microorganisms using a scalable, safe and cost effective method that consists of using a detonable or other reactive mixture 50 that can be repeatedly injected into a shock generation chamber 40 that is designed to contain detonation products and transmit shockwaves through a membrane 60 into a sterilization chamber 70 filled with the media 80 to be sterilized. As a non-limiting example of operational parameters of the apparatus 1 illustrated in FIG. 1 to FIG. 5 and FIG. 8 the shock generation section 40 of the apparatus 1 can be filled with a stoichiometric mixture of oxygen and natural gas at 20 atm initial pressure and ~0.03 g/cc initial density. This mixture is detonable thus initiation with spark plug 30 will cause detonation. The resulting detonation wave will create a shockwave in the shock generation section 40. Typically, a detonation wave propagating through a 20 atm detonable mixture will have ~60 MPa peak pressure, ~2 km/sec shock velocity, and ~0.2 g/cc density. This shockwave will reflect and transmit through the membrane 60 between the shock generation section 40 and the sterilization section 70 or will transmit through the walls for embodiments schematically shown in FIG. 5 and FIG. 8. The reflected shockwave will propagate back into the shock generation section 40 where it can reflect from the walls and be redirected toward the membrane 60. The transmitted shock will propagate through the membrane 60 into the sterilization section 70. The transmitted wave will have a shorter period. The wave period will also be a function of the duration of the positive phase of the detonation shock, which will in turn will be a function of the size and geometry of the shock generation section 40, and the parameters of the detonable mixture 50. The transmitted high amplitude acoustic wave will propagate in the media 80 and will reflect from the walls of the sterilization section 70 creating multiple high amplitude acoustic waves that will kill microorganisms such as bacteria in the media 80. The pressure and impulse of the transmitted acoustic and shockwaves will be sufficient for killing *Salmonella typhimurium, Blastocladiella emersonii, Escherichia coli* and similar microorganisms that can contaminate food and other products.

One of the critical advantages of the present invention includes without limitation its scalability to a wide range of sizes based on processing needs. The sizes of the shock generation section 40 and the sterilization section 70 in the embodiments schematically shown in FIGS. 1 through 8 can be selected to accommodate processing needs for sterilization. In a non-limiting example, the shock generation section 40 can be 1 ml to 100 ml in size in the apparatus for laboratory scale sterilization or 0.1 liter to 10 $m^3$ in size for industrial scale sterilization. In a non-limiting example, the volume of the sterilization section 70 can be 1 mil to 1 liter in size for small scale sterilization processes and 1 liter to 100 $m^3$ in volume for industrial scale sterilization processes. Based on processing needs, the shock generation section 40 and the sterilization section 70 may have one of the following: equal volumes; the shock generation section 40 may have a volume that is larger than the sterilization section 70; or the shock generation section 40 may have a volume that is smaller than that of the sterilization section 70.

The critical advantage of the present invention without limitation is its ability to generate shockwaves and acoustic waves with a wide range of parameters that will be beneficial for killing microorganisms without damaging the food or other material that is subjected to the sterilization and/or pasteurization process. The shock generation section 40 can be filled with a detonable reactants to provide a detonable mixture 50 with an initial density that may range from 0.1 to 1800 kg/$m^3$. Reaction of this mixture 50 in a detonative process or other rapid reaction process in the shock generation section 40 will generate shockwaves and/or acoustic waves in the sterilization section 70 with peak pressure in the range of 1 to 5000 mega pascals (MPa) and, preferably, between 10 and 2000 MPa.

The design of the shock generation section 40 can be implemented in various geometries that allow shockwave reflections and focusing or transmitting to a selected area of the sterilization section 70. The design of the sterilization section 70 can be implemented to allow focusing and multiple reflections of the transmitted shock waves that can enhance the efficiency of the sterilization.

To facilitate pressure containment and reflections of the shock wave the design of the parts of the shock generation section 40 that are not in contact with the media 80 can be made without limitation from materials with high strength and high impedance, such as metals, cermets, ceramics, polymers, fiber based composites, and combination thereof.

To facilitate pressure containment and transmission of the shock waves from the shock generation section 40 to the sterilization section 70, the membrane 60 and parts of the shock generation section 40 in contact with the media 80 to be sterilized can be made without limitations from materials with high strength and low impedance, such as polymers, suitable fiber-based composites, and thin high-strength materials such as steel and combinations thereof allowing wave transmission from the shock generation section 40 to the sterilization section 70 of the apparatus 1.

To facilitate multiple reflections of transmitted shock waves and acoustic waves that will increase sterilization effectiveness the walls of sterilization section 70 of the apparatus 1 according to the current invention can be made without limitation from materials with high impedance such as tungsten, tungsten carbide, steel, cermets, ceramics, and combinations thereof. To increase wave reflection effectiveness the wall thickness of the sterilization section 70 can be suitably selected by persons skilled in the art with the aid of no more than routine experimentation.

To produce multiple reflections of shockwaves and acoustic waves in the sterilization section 70 it is foreseen that the sterilization chamber geometry may have edges or asperities on the inner walls. Multiple reflections can be also be induced by adding high impedance materials to the volume containing media to be sterilized 80. For example, 1 cm diameter steel balls or 1 mm diameter solid particles of tungsten carbide can be added to media 80 in FIG. 1

To enhance killing the microorganisms in the sterilization section 70, bubbles of air or other gases may be introduced into the media to be sterilized 80 prior or during the sterilization process. The gas bubbles will reduce effective impedance of the media 80, produce additional sheer force on bacteria during and after shockwave propagation, and will produce additional shockwaves due to bubble collapse. All these effects will lead enhanced killing of microorganisms.

It is also understood that the design of the sterilization apparatus without limitation can include multiple shock generation sections 40*a*,40*b*,40*c* operating simultaneously or with a pre-determined time delay to sterilize media 80 in a single sterilization section 70. Also other designs can allow use of a single shock generation section 40 for sterilization of media 80 in multiple sterilization sections 70.

While particular embodiments of the present invention have been described and illustrated, it should be understood that the invention is not limited thereto since modifications may be made by persons skilled in the art. The present application contemplates any and all modifications that fall within the spirit and scope of the underlying invention disclosed and claimed herein.

What is claimed is:

1. A method for sterilization and pasteurization, comprising the steps of:
providing an apparatus comprised of a shock generation section; a sterilization section; and a membrane made of materials and dimensioned to facilitate containment of pressure in the shock generation section provided between the shock generation section and the sterilization section that seals the shock generation section and transmits shock waves and acoustic waves from the shock generation section into the sterilization section in use;
placing media contaminated with microorganisms into the sterilization section through continuous or intermittent injection;
introducing a mixture comprised of a detonable mixture or a reactive mixture that reacts to form a detonable mixture into the shock generation section;
causing formation of at least one of a shock wave and an acoustic wave within the shock generation section by igniting the detonable mixture or causing reaction of the reactive mixture so that the at least one of a shock wave and an acoustic wave impinges on the membrane and is transmitted thereby into the sterilization section, and so that the media is sterilized or pasteurized by the at least one of a shock wave and an acoustic wave that will kill at least some of the microorganisms;

venting reaction or detonation products from the shock generation section via a pressure relief valve; and repeating introducing the mixture and causing formation of at least one of a shock wave and an acoustic wave as many times as required for achieving a pre-determined degree of sterilization or pasteurization.

2. The method of claim 1, wherein the reactive mixture introduced into shock generation section undergoes at least one reaction selected from the group consisting of detonation, deflagration, transition from deflagration to detonation, rapid decomposition, and combinations thereof that results in rapid pressurization of the shock generation section.

3. The method of claim 1, wherein the sterilization section has a geometry that at least one of (a) allows focusing of the at least one of shock waves and acoustic waves transmitted from the shock generation section and (b) allows multiple reflections of the at least one of shock waves and acoustic waves, the geometry having at least one section selected from the group consisting of a variable cross section, a converging cross section, and any combination of converging and diverging cross section, so that the media to be sterilized will have increased exposure to the at least one of shock waves and acoustic waves.

4. The method of claim 1, wherein the shock generation section has a geometry selected from the group consisting of a converging geometry, a diverging geometry, and any combination of converging and diverging geometries that allows focusing of the at least one of a shock wave and an acoustic wave transmitted into the sterilization section.

5. The method of claim 1, wherein walls of the shock generation section and the membrane are made of solid materials that facilitate containment of pressure and have a thickness that is larger than 0.5 mm and a shape that is one of cylindrical, hemispherical, spherical, or a combination thereof, and wherein walls of the sterilization section have a shape that is one of cylindrical, hemispherical, spherical, or a combination thereof.

6. The method of claim 1, where the media to be sterilized is introduced into and removed from the sterilization section in a mode that is one of continuous, intermittent, or batchwise.

7. The method of claim 1, wherein the walls of the shock generation section are composed of materials that facilitate containment of pressure and at least partially transmits at least one of shock waves and acoustic waves, and wherein the walls of the shock generation section are at least partially immersed within the media contaminated with microorganisms contained within the sterilization section.

8. The method of claim 1, further comprising introducing bubbles of air or other gases into the media to be sterilized contained within the sterilization section to enhance killing of microorganisms due to liquid motion created by gas bubble collapse and expansion when at least one of acoustic waves and shock waves are transmitted from the shock generation section into the sterilization section.

9. A method for sterilization and pasteurization, comprising the steps of:

providing an apparatus comprised of a shock generation section; a sterilization section; wherein the external walls of the shock generation section are at least partially immersed in the media to be sterilized, wherein the external walls of the shock generation section are composed of materials and dimensioned to facilitate containment of pressure and at least partially transmits at least one of the shock waves and acoustic waves;

placing media contaminated with microorganisms into the sterilization section through continuous or intermittent injection;

introducing a mixture comprised of a detonable mixture or a reactive mixture that reacts to form a detonable mixture into the shock generation section;

causing formation of at least one of a shock wave and an acoustic wave within the shock generation section by igniting the detonable mixture or causing reaction of the reactive mixture so that the at least one of a shock wave and an acoustic wave impinges on the walls and is transmitted thereby into the sterilization section, and so that the media is sterilized or pasteurized by the at least one of a shock wave and an acoustic wave that will kill at least some of the microorganisms;

venting reaction or detonation products from the shock generation section via a pressure relief valve; and repeating introducing the mixture and causing formation of at least one of a shock wave and an acoustic wave as many times as required for achieving a pre-determined degree of sterilization or pasteurization.

10. The method of claim 9, where the media to be sterilized is introduced into and removed from the sterilization section in a mode that is one of continuous, intermittent, or batchwise.

11. The method of claim 9, wherein the shock generation section is composed of multiple chambers wherein the external walls of the shock generation chambers are at least partially immersed within the media contained within the sterilization section, wherein the external walls of the multiple chambers are composed of materials and dimensioned to facilitate containment of pressure and at least partially transmits at least one of the shock waves and acoustic waves, and wherein igniting the detonable mixture or causing reaction of the reactive mixture within the respective chambers is performed simultaneously or sequentially in a timed manner with respect to one another.

12. The method of claim 9, further comprising introducing bubbles of air or other gases into the media to be sterilized contained within the sterilization section.

* * * * *